(12) United States Patent
Bhavarisetti et al.

(10) Patent No.: US 9,622,979 B2
(45) Date of Patent: Apr. 18, 2017

(54) MULTILAYERED DOSAGE FORM

(75) Inventors: Murali Krishna Bhavarisetti, Krishna (IN); Kumaravel Vivek, Chennai (IN); Sreekanth Narravula, Guntur (IN); Romi Barat Singh, Varanasi (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 14/129,612

(22) PCT Filed: Jun. 29, 2012

(86) PCT No.: PCT/IB2012/053341
§ 371 (c)(1),
(2), (4) Date: Oct. 8, 2014

(87) PCT Pub. No.: WO2013/001516
PCT Pub. Date: Jan. 3, 2013

(65) Prior Publication Data
US 2015/0132378 A1    May 14, 2015

(30) Foreign Application Priority Data
Jun. 29, 2011 (IN) .......................... 1841/DEL/2011

(51) Int. Cl.
| A61K 9/24 | (2006.01) |
| A61K 31/138 | (2006.01) |
| A61K 31/366 | (2006.01) |
| A61K 31/445 | (2006.01) |
| A61K 31/554 | (2006.01) |
| A61K 31/137 | (2006.01) |
| A61K 31/455 | (2006.01) |
| A61K 31/55 | (2006.01) |
| A61K 9/20 | (2006.01) |

(52) U.S. Cl.
CPC ............ *A61K 9/209* (2013.01); *A61K 9/2009* (2013.01); *A61K 9/2018* (2013.01); *A61K 9/2027* (2013.01); *A61K 9/2054* (2013.01); *A61K 31/137* (2013.01); *A61K 31/138* (2013.01); *A61K 31/366* (2013.01); *A61K 31/445* (2013.01); *A61K 31/455* (2013.01); *A61K 31/55* (2013.01); *A61K 31/554* (2013.01)

(58) Field of Classification Search
CPC ........................................................ A61K 9/20
USPC ........................................................ 424/464
See application file for complete search history.

(56) References Cited

U.S. PATENT DOCUMENTS

| 5,221,278 | A | 6/1993 | Linkwitz et al. .......... 604/890.1 |
| 5,318,558 | A | 6/1994 | Linkwitz et al. .......... 604/892.1 |
| 5,549,913 | A * | 8/1996 | Colombo ............... A61K 9/209 424/458 |
| 5,626,874 | A | 5/1997 | Conte et al. .................. 424/464 |
| 5,783,212 | A | 7/1998 | Fassihi et al. ................. 424/472 |
| 6,183,778 | B1 | 2/2001 | Conte et al. .................. 424/472 |
| 6,797,283 | B1 | 9/2004 | Edgren et al. ................. 424/472 |
| 6,919,373 | B1 * | 7/2005 | Lam .................... A61K 9/0004 514/532 |
| 7,387,793 | B2 | 6/2008 | Venkatesh et al. ........... 424/489 |
| 2008/0274182 | A1 * | 11/2008 | Alida Boekema et al. .. 424/480 |
| 2010/0040681 | A1 | 2/2010 | Park et al. .................... 424/472 |

FOREIGN PATENT DOCUMENTS

| EP | 0 631 775 | 8/1999 | .............. A61K 9/20 |
| IT | WO 03075897 A1 * | 9/2003 | .......... A61K 9/2072 |
| WO | WO 03/075897 | 9/2003 | .............. A61K 9/28 |
| WO | WO 03075897 A1 * | 9/2003 | |

\* cited by examiner

*Primary Examiner* — Gollamudi Kishore
*Assistant Examiner* — Amanda Heyes

(57) ABSTRACT

The present invention relates to a multilayered coated tablet comprising at least three layers, i.e., first, second and third layer wherein the first and third layers contain at least one active pharmaceutical ingredient and the second layer is either a placebo or an immediate-release drug layer. Further, the tablet has a delayed-release coating, wherein the coating may contain one or more pore-forming agents and/or orifices on one or both sides. Furthermore, it may contain an immediate-release layer of the drug over the delayed-release coating layer. The present invention further relates to processes for preparing such a multilayered coated tablet.

21 Claims, No Drawings

MULTILAYERED DOSAGE FORM

FIELD OF THE INVENTION

The present invention relates to a multilayered coated tablet comprising at least three layers, i.e., first, second and third layer wherein the first and third layers contain at least one active pharmaceutical ingredient and the second layer is either a placebo or an immediate-release drug layer. Further, the tablet has a delayed-release coating, wherein the coating may contain one or more pore-forming agents and/or orifices on one or both sides. Furthermore, it may contain an immediate-release layer of the drug over the delayed-release coating layer. The present invention further relates to processes for preparing such a multilayered coated tablet.

BACKGROUND OF THE INVENTION

Oral drug delivery continues to be the most popular route of administration due to its versatility, ease of administration and patient compliance. An oral medication that improves compliance, and thus results in more effective treatment, has been one of the major drivers of innovation in the oral drug delivery market.

Modified-release or a controlled-release dosage form is an advancement in the oral drug delivery which has led to improved patient compliance and reduced side effects of the drugs. "Modified-release" means that the release of the drug from the dosage form has been modified in some way with respect to an immediate-release delivery of the same drug. Usually, this is to slow the release of the drug so that the medicine doesn't have to be taken too often and therefore improves compliance. The other benefit from modifying-release is that the drug release is controlled and there are smaller peaks and troughs in blood levels, therefore reducing the chance of peak effects and increasing the likelihood of therapeutic effectiveness for longer periods of time.

Generally, controlled-release systems can be categorized into two groups based on actions. Extended-release formulations deliver a portion of the total dose shortly after ingestion and the remainder over an extended time frame. Delayed-release systems provide steady dosing after passage through the stomach. Controlled-drug delivery systems aim to maintain plasma concentration of drugs within the therapeutic window for a longer period of time, thereby to ensure sustained therapeutic action.

Further manipulation of delivery systems has led to the development of chronotherapeutic systems, where release enables a drug to take advantage of the natural biorhythms of the human body. Pulsatile drug delivery system provides a chronotherapeutic release to meet the needs of patients suffering from diseases which follow the biological rhythm, such as asthma, where episodes of attack mostly happen late at night or rheumatoid arthritis, where the pain peaks at the morning. Pulsatile drug delivery systems are characterized by at least two distinctive drug-release phases following a predetermined lag time. Drug's release may be controlled by time, by site or a combination of the two parameters.

Two of the most widely commercialized controlled-release technologies are Oros® (developed by Alza), and the Sodas® technology developed by Elan. Other successfully commercialized technologies include SkyePharma's Geomatrix®, Eurand's Diffucaps® and Elan's Codas®.

U.S. Pat. Nos. 5,318,558 and 5,221,278, assigned to Alza, claim the pulsatile delivery of agents from osmotic systems based on the technology of an expandable orifice.

U.S. Pat. No. 7,387,793, assigned to Eurand, relates to a multi-particulate pharmaceutical dosage form wherein the active drug is layered onto a neutral core (such as cellulose spheres) and then one or more rate-controlling, functional membranes are applied.

U.S. Pat. No. 6,797,283, assigned to Alza, relates to a multilayered dosage form comprising: a first layer comprising an amount of swellable polymer, said amount being sufficient to swell said first layer such that the active agent dosage form is retained within a stomach of a subject; a second layer laminated with the first layer at a common surface, said second layer comprising a therapeutic amount of an active agent and being formulated to swell to a lesser extent than the first layer; and at least one band of insoluble material circumscribing only a portion of said first layer and said second layer, said at least one band of insoluble material binding together the first layer and the second layer.

U.S. Pat. No. 6,183,778, assigned to Jagotec AG, relates to an oral dosage form in the form of a tablet, capable of providing one or more pharmaceutically active substances in two or more different releases, the dosage form comprising at least three layers of specific geometric shape, wherein the dosage form comprises:

a) a first layer from which there occurs a first release of at least one pharmaceutically active substance, wherein the release is characterized as an immediate-release or a controlled-release, the layer comprising substances which swell or solubilize when contacted with aqueous liquids;

b) a second layer from which there occurs a second release of at least one pharmaceutically active substance, wherein the at least one pharmaceutically active substance is the same as or different from the at least one pharmaceutically active substance released from the first layer in the first release, wherein the second release is characterized as a controlled-release, the second layer comprising substances that swell, or erode, or are gellable when contacted with aqueous liquids; and c) a third layer at least partially coating one or more free surfaces of the second layer, the third layer comprising substances that swell, or erode, or are gellable when contacted with aqueous liquids, and wherein at least two layers of the dosage form are formed by the compression of a mixture of granular components.

U.S. Pat. No. 5,783,212, assigned to Temple University of the Commonwealth System of Higher Education, discloses a multilayer tablet for release of active pharmaceutical ingredient at a constant rate with a zero order kinetic profile, in which two outer layers contain swellable and erodible polymers, an inner layer contains an active pharmaceutical ingredient and swellable and erodible polymers, and each layer differs in composition and thickness.

U.S. Pat. No. 5,626,874, assigned to Ekita Investments N.V., discloses a multilayer tablet consisting of two outer layers containing gellable or erodible polymers and an inner layer containing an active ingredient. The side surface of the inner layer occupies about 5% to 35% of the tablet's total surface.

U.S. Publication No. 2010/0040681, filed by GL Pharmtech Corp., relates to an oral sustained-release triple layer tablet, more particularly, a triple layer tablet consisting of an inner immediate-release layer containing an active pharmaceutical ingredient and two outer layers containing swellable polymers. On exposure to aqueous media, the two outer layers swell to form gelled layers surrounding the lateral side of the inner layer rapidly, thereby controlling effectively the release of drug from the inner immediate-release layer.

U.S. Pat. No. 5,549,913, assigned to Inverni Della Beffa S.p.A., discloses a multilayer tablet for release of active pharmaceutical ingredient at a constant rate with a zero order kinetic profile, in which two outer layers contain active pharmaceutical ingredient and hydrophilic polymers, and an inner layer contains a water-soluble polymer without the active pharmaceutical ingredient. The inner layer is readily dissolved in aqueous media to separate the two outer layers, and thus to increase the surface area of the matrix.

The present inventors have developed a novel multilayered coated tablet comprising at least three layers, wherein the first and third layers contain at least one active pharmaceutical ingredient and the second layer is either a placebo or an immediate-release drug layer. This tablet further comprises a delayed-release coating wherein the coating may contain one or more pore-forming agents and/or orifices on one or both sides. Further, there may be an immediate-release layer over the delayed-release coating for an initial pulse. The orifice or pore-forming agents present in the coating lead to an initial hydration and slow-release of the drug until the time it reaches the intestine. After reaching the intestine, the delayed-release coating and the second placebo or drug layer dissolve or erode separating the first and third drug layers. The first and third drug layers of the dosage form can be two extended-release layers or one immediate-release layer and another extended-release layer. The present dosage form also provides the pulsatile-release of the drug by the delivery of the drug from two or three different layers with different release rates. Further, the present dosage form can be used to formulate two incompatible drugs into a single tablet, wherein the second layer will prevent the two drugs from coming in contact with each other.

SUMMARY OF THE INVENTION

The present invention relates to a multilayered coated tablet.

One aspect of the present invention relates to a multilayered coated tablet, comprising at least three layers wherein:
a) the first and third layers contain an active pharmaceutical ingredient; and
b) the second layer is either a placebo layer or contains active pharmaceutical ingredient.

According to one of the embodiments of the present invention, the first and third layers contain the same drug.

According to another embodiment of the present invention, the first and third layers contain different drugs.

According to another embodiment of the present invention, at least one of the first and third layers provides an extended-release of drug.

According to yet another embodiment of the present invention, the first layer provides an immediate-release of the drug and the third layer provides an extended-release of the drug.

According to yet another embodiment of the present invention, the first layer provides an extended-release of the drug and the third layer provides an immediate-release of the drug.

According to another embodiment of the present invention, the second layer is a placebo layer.

According to yet another embodiment of the present invention, the second layer is water-soluble or water-swellable or water-insoluble and helps in the division of the tablet into different layers.

According to another embodiment of the present invention, the second layer comprises microcrystalline cellulose, corn starch, povidone, magnesium stearate, talc or lactose and optionally a drug.

According to yet another embodiment of the present invention, the second layer comprises an immediate-release drug layer.

According to another embodiment of the present invention, the three layers contain the same drug.

According to another embodiment of the present invention, the three layers contain different drugs.

According to another embodiment of the present invention, two of the layers contain the same drug and the third layer contains a different drug.

According to another embodiment of the present invention, the coating on the said multilayered tablet is a delayed-release coating.

According to another embodiment of the present invention, the delayed-release coating contains an orifice on one side of the tablet.

According to another embodiment of the present invention, the delayed-release coating contains an orifice on both sides of the tablet.

According to another embodiment of the present invention, the delayed-release coating contains at least one pore-forming agent.

According to another embodiment of the present invention, the delayed-release coating contains an orifice on one side of the tablet and a pore-forming agent.

According to another embodiment of the present invention, the delayed-release coating contains an orifice on both sides of the tablet and a pore-forming agent.

According to another embodiment of the present invention, the pore-forming agent used in the delayed-release coating is selected from hydrophilic, hydrophobic, or a combination of both hydrophilic and hydrophobic substances such as sodium chloride, potassium chloride, and magnesium salts, lactose, sucrose, sorbitol, and mannitol, polyvinyl alcohols and glycols, such as polyethylene glycol and propylene glycol; hydroxypropyl celluloses, hydroxy propyl methycelluloses; methacrylic acid copolymers; croscarmellose sodium, crospovidone sodium starch glycolate, talc, silicon dioxide, polyvinylpyrrolidones, gelling agents such as carbopol, xanthan gum; or mixtures thereof.

According to another embodiment of the present invention, the delayed-release polymer used in the delayed-release coating is selected from cellulose acetate phthalate (CAP), cellulose acetate trimelletate (CAT), poly(vinyl acetate)phthalate (PVAP), hydroxypropyl methylcellulose phthalate (HPMCP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, (Eudragit®-L-30-D, Eudragit®L100-55), Eudragit® L100, Eudragit® L12,5, Eudragit® S100, Eudragit® S12,5), Poly(methyl acrylate-co-methyl methacrylate-co-methacrylic acid) 7:3:1— (Eudragit® FS30D) hydroxypropyl methylcellulose acetate succinate (HPMCAS), and combinations thereof.

According to another embodiment of the present invention, the delayed-release coating further comprises an immediate-release drug layer over it.

According to another embodiment of the present invention, the immediate-release drug layer over the delayed-release coating layer may contain the same drug as those in any of the internal layers of the tablet.

According to another embodiment of the present invention, the immediate-release layer over the delayed-release coating layer may contain a drug different than those in any of the internal layers of the tablet.

According to another embodiment of the present invention, the shape of the tablet is capsular, circular or cylindrical.

According to another aspect of the present invention, the multilayered coated tablet of the present invention further comprises pharmaceutically acceptable excipients selected from the group comprising adsorbents, antioxidants, acidifying agents, alkalizing agents, buffering agents, colorants, flavorants, sweetening agents, antiadherents, binders, diluents, direct compression excipients, disintegrants, glidants, lubricants opaquants and/or polishing agents.

According to another aspect of the present invention, the multilayered coated tablet of the present invention is prepared by blending or dry granulating or wet granulating pharmaceutically active agent of the first and the third layers with one or more excipients and blending inert excipients of the second layer and finally compressing the three blends into a tri-layered tablet, which is further coated using the coating dispersion of the delayed-release polymer. And by further drilling an orifice on one or both the sides of the tablet.

According to another aspect of the present invention, the multilayered coated tablet of the present invention is prepared by blending or dry granulating or wet granulating pharmaceutically active agent of the first, second and the third layers with one or more excipients and finally compressing the three blends into a tri-layered tablet, coating using the coating dispersion of the delayed-release polymer, further drilling an orifice on one or both the sides of the tablet and finally layering an immediate-release drug layer over the delayed-release coating.

DETAILED DESCRIPTION OF THE INVENTION

The present invention relates to a novel multilayered coated tablet having at least three layers, i.e., first, second and third layer.

The phrase "multilayered coated tablet", as used herein, relates to a tablet having more than two layers. More particularly, it relates to a tablet having three layers.

The phrase "active pharmaceutical ingredient", as used herein, relates to any therapeutic or diagnostic agent now known or hereinafter discovered that can be formulated as described herein.

The active pharmaceutical ingredient may be selected from the group consisting of pharmaceutically acceptable organic or inorganic compounds including analgesics, anticonvulsants, anesthetics, antidiabetic agents, anti-infective agents, antineoplastics, antiparkinsonian agents, antirheumatic agents, cardiovascular agents, central nervous system stimulants, dopamine receptor agonists, gastrointestinal agents, psychotherapeutic agents, or urinary tract agents.

Suitable examples of drugs which can be incorporated into the dosage form of the present invention include, but are not limited to, albuterol sulfate, amoxicillin, bupropion hydrochloride, carbidopa, cefaclor, diclofenac sodium, erythromycin, felodipine, loratidine, lithium carbonate, methylphenidate, metaprolol tartrate, nifedipine, propranolol, verapamil hydrochloride, omeprazole, sotalol hydrochloride, theophylline, terbutaline sulphate, enalapril, diltiazem, nifedipine, lovastatin, simvastatin, ibuprofen, indomethacin, tenoxicam, and acetylsalicylic acid.

The term "pharmaceutically acceptable excipient" is intended to denote any material which is inert in the sense that it substantially does not have any therapeutic and/or prophylactic effect per se. Such an excipient may be added with the purpose of making it possible to obtain a pharmaceutical composition which has acceptable technical properties.

As used herein, the term "alkalizing agent" is intended to mean a compound used to provide alkaline medium for product stability.

As used herein, the term "acidifying agent" is intended to mean a compound used to provide an acidic medium for product stability.

The multilayered coated tablet of the present invention comprises at least three layers; first, second and third layer; wherein the said first and third layers are drug layers and second layer is either a placebo or an immediate-release drug layer. This tablet further comprises a delayed-release coating wherein the coating may contain one or more pore-forming agents and/or orifices on one or both sides. Further, there may be an immediate-release layer over the delayed-release coating for an initial pulse. The orifice or pore-forming agents present in the coating lead to an initial hydration and slow-release of the drug until the time it reaches the intestine. The incorporation of the pore-forming agents or the orifices in the polymer coating allows for a release of the medicament in the stomach for immediate-release and thereafter release additional medicament in the intestines for delayed-release. After reaching the intestine, the delayed-release coating and the second placebo or drug layer dissolves or erodes, separating the first and third drug layers.

The two drug layers of the dosage form can be two extended-release layers or one immediate-release layer and another extended-release layer. The present dosage form also provides for the pulsatile-release of the drug by the delivery of the drug from two different layers with different release rates. Further, the present dosage form can be used to formulate two incompatible drugs into a single tablet wherein the second layer will prevent the two drugs from coming in contact with each other.

The multilayered coated tablet of the present invention further comprises pharmaceutically acceptable excipients selected from the group comprising binders, diluents, direct compression excipients, disintegrants, glidants, lubricants, antioxidants, acidifying agents, alkalizing agents, colorants, flavorants, sweetening agents, antiadherents, and plasticizers.

Suitable examples of binders include, but are not limited to, polyvinylpyrrolidone, starch mucilage, pregelatinized starch, sodium alginate, alginic acid, acacia mucilage, tragacanth, hydroxypropylmethyl cellulose, carboxymethylcellulose sodium, carboxymethylcellulose calcium, microcrystalline cellulose, ethyl cellulose, polyethylene glycol, hydroxyethyl cellulose, hydroxy propyl cellulose, methyl cellulose, polymethacrylates, carboxyvinyl polymers, carbopols, and combinations thereof.

Suitable examples of diluents include, but are not limited to, corn starch, lactose, white sugar, sucrose, sugar compressible, sugar confectioners, glucose, sorbitol, calcium carbonate, calcium phosphate-dibasic, calcium phosphate-tribasic, calcium sulfate, microcrystalline cellulose, silicified microcrystalline cellulose, cellulose powdered, dextrates, dextrins, dextrose, fructose, kaolin, lactitol, mannitol, starch, pregelatinized starch, or mixtures thereof.

Suitable examples of disintegrants include, but are not limited to, cross-linked polyvinylpyrrolidone, sodium starch glycolate, cross-linked sodium carboxymethyl cellulose (crosscarmellose sodium), calcium carboxymethyl cellulose, alginic acid and alginates, pregelatinised starch, starch and starch derivatives, low-substituted hydroxypropyl cellulose, and combinations thereof.

Examples of lubricants and glidants include, but are not limited to, colloidal anhydrous silica, stearic acid, magnesium stearate, calcium stearate, talc, hydrogenated castor oil, sucrose esters of fatty acids, microcrystalline wax, yellow beeswax, white beeswax, or mixtures thereof.

Suitable examples of direct compression excipients include, but are not limited to, dibasic calcium phosphate, microcrystalline cellulose, lactose, mannitol, or mixtures thereof.

Examples of antioxidants include, but are not limited to, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate and sodium metabisulfite, or mixtures thereof.

Suitable examples of alkalizing agents include, but are not limited to, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids and trolamine.

Suitable examples of acidifying agents include, but are not limited to, acetic acid, acidic amino acids, citric acid, fumaric acid and other alpha hydroxy acids, hydrochloric acid, ascorbic acid, phosphoric acid, sulfuric acid, tartaric acid and nitric acid.

Examples of plasticizers include triethyl citrate, tributyl citrate, triacetin, polyethylene glycol, propylene glycol, diethylphthatate and oils/glycerides such as fractionated coconut oil or castor oil, and any combination thereof.

Coloring agents and flavoring agents may be selected from any FDA approved colors and flavors for oral use.

The pharmaceutical compositions of the present invention may optionally contain surfactants.

Surfactants/wetting agents include both non-ionic and ionic (cationic, anionic and zwitterionic) surfactants suitable for use in pharmaceutical compositions. These include but are not limited to, polyethoxylated fatty acid esters, polyethylene glycol fatty acid esters, alcohol-oil transesterification products, polyglycerized fatty acids, polyethylene glycol sorbitan fatty acid esters, sugar esters, polyoxyethylene-polyoxypropylene block copolymers, ionic surfactants, derivatives of fat-soluble vitamins, and mixtures thereof. Suitable examples include sodium lauryl sulphate, sodium dodecyl sulphate, polyoxyethylene castor oil derivatives, for example, tweens, polyoxyethylene-polyoxypropylene block copolymers, for example, poloxamer, or mixtures thereof.

Suitable extended-release polymers may be selected from one or more of water-miscible polymers, water-insoluble polymers, oils and oily materials, and mixtures thereof.

The water-miscible polymer may be selected from one or more of hydroxypropyl methylcellulose, hydroxypropyl cellulose, methylcellulose, sodium carboxymethylcellulose, hydroxyethyl cellulose and other cellulose derivatives, polymethacrylic copolymer, poloxamers, polyoxyethylene stearate, polyvinylpyrrolidone, polyvinylpyrrolidone-polyvinylacetate copolymer (PVP-PVA), polyvinyl alcohol, polyethylene oxide, and mixtures thereof.

The water-insoluble polymer may be selected from one or more of ethyl cellulose, cellulose acetate, cellulose nitrate, and mixtures thereof.

The oil or oily material may be hydrophilic or hydrophobic oil or oily material or their mixtures. Hydrophilic oil or oily material may be polyether glycols such as polypropylene glycols; polyoxyethylenes; polyoxypropylenes; poloxamers; polyglycolized glycerides such as gelucire and mixtures thereof. Hydrophobic oil or oily material may be straight chain saturated hydrocarbons; sorbitan esters such as sorbitan di isostearate, sorbitan dioleate, sorbitan monolaurate, sorbitan monoisostearate, sorbitan monooleate, sorbitan monopalmitate, sorbitan monostearate, sorbitan sesqui-isostearate, sorbitan sesquioleate, sorbitan sesquistearate, sorbitan tri-isostearate, sorbitan trioleate, sorbitan tristearate; higher fatty acid such as stearic acid, myristic acid, palmitic acid; higher alcohols such as cetanol, stearyl alcohol; waxes such as glyceryl monostearate, glyceryl monooleate, hydrogenated tallow, myristyl alcohol, stearyl alcohol, yellow beeswax, white beeswax, carnauba wax, castor wax, Japan wax; substituted and/or unsubstituted mono, di or triglycerides; NVP polymers; PVP polymers; acrylic polymers, and mixtures thereof.

Delayed-release material (coating) used in the multilayered tablet of the invention will possess limited solubility or erodibility or be insoluble or non-erodible in a first external fluid, i.e., gastric juices, while being soluble and/or erodible in a second external fluid, such as intestinal juices.

Suitable examples of such polymeric materials include, but are not limited to, cellulose acetate phthalate (CAP), cellulose acetate trimelletate (CAT), poly(vinyl acetate) phthalate (PVAP), hydroxypropyl methylcellulose phthalate (HPMCP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, Eudragit®L-30-D (MA-EA, 1:1), Eudragit® L-100-55 (MA-EA, 1:1), Eudragit® L100, Eudragit® L12,5, Eudragit® S100, Eudragit® S12,5, Poly (methyl acrylate-co-methyl methacrylate-co-methacrylic acid) 7:3:1—(Eudragit® FS30D) hydroxypropyl methylcellulose acetate succinate, Coateric®(PVAP), Aquateric® (CAP), Aqoat® (HPMCAS), and combinations thereof.

The pore-forming agent used in the delayed-release coating is selected from hydrophilic, hydrophobic, or a combination of both hydrophilic and hydrophobic, substances such as sodium chloride, potassium chloride, and magnesium salts, lactose, sucrose, sorbitol, and mannitol, polyvinyl alcohols and glycols, such as polyethylene glycol and propylene glycol; hydroxypropyl celluloses, hydroxy propyl methylcelluloses; methacrylic acid copolymers; croscarmellose sodium, crospovidone sodium starch glycolate, talc, silicon dioxide, polyvinylpyrrolidones, gelling agents such as carbopol, and xanthan gum; and any mixtures thereof.

An orifice was drilled in the coating using laser drilling either on one side of the tablet or on both sides.

The blend for multilayered tablet of the present invention is prepared by dry mixing or dry granulation or wet granulation or any other process known in the art. Finally compressing the three blends into a tri-layered tablet, which is further coated using the coating dispersion of the delayed-release polymer. Then drilling an orifice on one or both sides of the tablet. Further, the delayed-release coating may be layered with an optional immediate-release drug layer.

The following examples represent various embodiments according to the present invention. The examples are given solely for the purpose of illustration and are not to be construed as liming the present invention in any way, as many other variations thereof are possible within the scope of the invention.

Example 1

| S. No. | Ingredients | Percent (%) w/w (total weight of the dosage form) |
|---|---|---|
| | First Layer: | |
| 1. | Diltiazem HCl | 5.29 |
| 2. | Hydroxypropylmethylcellulose | 7.94 |
| 3. | Lactose anhydrous | 14.56 |
| 4. | Talc | 0.265 |
| 5. | Magnesium stearate | 0.265 |
| | Second Layer: | |
| 1. | Lactose anhydrous | 23.16 |
| 2. | Magnesium stearate | 0.265 |
| 3. | Talc | 0.265 |
| | Third Layer: | |
| 1. | Diltiazem HCl | 10.59 |
| 2. | Hydroxypropylmethylcellulose | 14.56 |
| 3. | Lactose anhydrous (DCL 21) | 13.23 |
| 4. | Talc | 0.265 |
| 5. | Magnesium stearate | 0.265 |
| | Coating: | |
| 1. | Eudragit ® L30D-55* | 6.99 |
| 2. | Triethyl citrate | 1.40 |
| 3. | Talc | 0.70 |
| 4. | Purified water | Qs |

Process

First Layer:
1. Sieve diltiazem HCl, hydroxypropylmethylcellulose and lactose and then blend them together.
2. Then pass talc and magnesium stearate through sieve and transfer the mixture to the blender of step 1.

Second Layer:
1. Sieve lactose, talc and magnesium stearate and then blend them together.

Third Layer:
1. Sieve diltiazem HCl, hydroxypropylmethylcellulose and lactose and blend them with each other.
2. Then pass talc and magnesium stearate through sieve and transfer the mixture to the blender of step 1.

Finally, compress all three layers into a tablet.

Coating:
1. Disperse talc in purified water.
2. Add triethyl citrate to the mixture of step 1.
3. Further add Eudragit® L30D-55 to the above dispersion while stirring slowly.
4. Coat the compressed tablets using the coating dispersion of step 3.
5. Finally, drill the orifice on one of the sides of the coated tablet.

Example 2

| S. No. | Ingredients | Percent (%) w/w (total weight of the dosage form) |
|---|---|---|
| | First Layer: | |
| 1. | Diltiazem HCl | 6.55 |
| 2. | Carbopol 974P | 6.55 |
| 3. | Lactose anhydrous | 15.71 |
| 4. | Talc | 0.262 |
| 5. | Magnesium stearate | 0.262 |
| | Second Layer: | |
| 1. | Lactose anhydrous (DCL 21) | 18.33 |
| 2. | Magnesium stearate | 0.262 |
| 3. | Talc | 0.262 |
| | Third Layer: | |
| 1. | Diltiazem HCl | 9.16 |
| 2. | Hydroxypropylmethylcellulose | 13.09 |
| 3. | Lactose anhydrous | 18.33 |
| 4. | Talc | 0.262 |
| 5. | Magnesium stearate | 0.262 |
| | Coating | |
| 1. | Eudragit ® L30D-55* | 6.70 |
| 2. | Triethyl citrate | 1.00 |
| 3. | Talc | 1.00 |
| 4. | Polyvinylpyrrolidone | 2.00 |
| 5. | Purified water | qs |

Process

First Layer:
1. Sieve diltiazem HCl, carbopol and lactose and blend them together.
2. Then pass talc and magnesium stearate through sieve and transfer the mixture to the blender of step 1.

Second Layer:
1. Sieve lactose, talc and magnesium stearate and then blend them together.

Third Layer:
1. Sieve diltiazem, HCl, hydroxypropylmethylcellulose and lactose and blend them with each other.
2. Then pass talc and magnesium stearate through sieve and transfer the mixture to the blender of step 1.

Finally, compress all three layers into a tablet.

Coating:
1. Disperse talc in purified water.
2. Add polyvinylpyrrolidone and triethyl citrate to the mixture of step 1.
3. Further add Eudragit® L30D-55 to the above dispersion while stirring slowly.
4. Then coat compressed tablets using the coating dispersion of step 3.

Example 3

| S. No. | Ingredients | Percent (%) w/w (total weight of the dosage form) |
|---|---|---|
| | First Layer: | |
| 1. | Propranolol HCl | 5.49 |
| 2. | Hydroxypropylmethylcellulose | 8.24 |
| 3. | Lactose anhydrous (DCL 21) | 15.11 |
| 4. | Talc | 0.275 |
| 5. | Magnesium stearate | 0.275 |
| | Second Layer: | |
| 1. | Lactose anhydrous (DCL 21) | 19.23 |
| 2. | Magnesium stearate | 0.275 |
| 3. | Talc | 0.275 |
| | Third Layer: | |
| 1. | Propranolol HCl | 10.99 |
| 2. | Hydroxypropylmethylcellulose | 15.11 |

-continued

| S. No. | Ingredients | Percent (%) w/w (total weight of the dosage form) |
|---|---|---|
| 3. | Lactose anhydrous (DCL 21) | 15.11 |
| 4. | Talc | 0.275 |
| 5. | Magnesium stearate | 0.275 |
| Coating | | |
| 1. | Eudragit ® L30D-55* | 7.27 |
| 2. | Triethyl citrate | 1.10 |
| 3. | Talc | 0.73 |
| 4. | Purified water | Qs |

Process
First Layer:
1. Sieve propranolol HCl, hydroxypropylmethylcellulose and lactose and blend them together.
2. Then pass talc and magnesium stearate through sieve and transfer the mixture to the blender of step 1.
Second Layer:
1. Sieve lactose, talc and magnesium stearate and then blend them together.
Third Layer:
1. Sift propranolol HCl, hydroxypropylmethylcellulose and lactose and blend them with each other.
2. Then pass talc and magnesium stearate through sieve and transfer the mixture to the blender of step 1.
Finally, compress all three layers into a tablet.
Coating:
1. Disperse talc in purified water.
2. Add triethyl citrate to the mixture of step 1.
3. Further add Eudragit® L30D-55 to the above dispersion while stirring slowly.
4. Then coat compressed tablets using the coating dispersion of step 3.
5. Finally, drill the orifice on both sides of the coated tablet.

Example 4

| S. No. | Ingredients | Percent (%) w/w (total weight of the dosage form) |
|---|---|---|
| First Layer: | | |
| 1. | Propranolol HCl | 5.49 |
| 2. | Hydroxypropylmethylcellulose | 8.24 |
| 3. | Lactose anhydrous (DCL 21) | 15.11 |
| 4. | Talc | 0.275 |
| 5. | Magnesium stearate | 0.275 |
| Second Layer: | | |
| 1. | Lactose anhydrous (DCL 21) | 19.23 |
| 2. | Magnesium stearate | 0.275 |
| 3. | Talc | 0.275 |
| Third Layer: | | |
| 1. | Propranolol HCl | 10.99 |
| 2. | Hydroxypropylmethylcellulose | 12.36 |
| 3. | Lactose anhydrous (DCL 21) | 17.85 |
| 4. | Talc | 0.275 |
| 5. | Magnesium stearate | 0.275 |
| Coating | | |
| 1. | Eudragit ® L30D-55* | 6.06 |
| 2. | Polyvinylpyrrolidone | 1.51 |
| 3. | Triethyl citrate | 0.90 |
| 4. | Talc | 0.61 |
| 5. | Purified water | Qs |

Process
First Layer:
1. Sieve propranolol HCl, hydroxypropylmethylcellulose and lactose and blend them together.
2. Then pass talc and magnesium stearate through sieve and transfer the mixture to the blender of step 1.
Second Layer:
1. Sieve lactose, talc and magnesium stearate and then blend them together.
Third Layer:
1. Sieve propranolol HCl, hydroxypropylmethylcellulose and lactose and blend them with each other.
2. Then pass talc and magnesium stearate through sieve and transfer the mixture to the blender of step 1.
Finally, compress all three layers into a tablet.
Coating:
1. Disperse talc in purified water.
2. Add polyvinylpyrrolidone and triethyl citrate to the mixture of step 1.
3. Further add Eudragit® L30D-55 to the above dispersion while stirring slowly.
4. Then coat the compressed tablets using the coating dispersion of step 3.

Example 5

| S. No. | Ingredients | Percent (%) w/w (total weight of the dosage form) |
|---|---|---|
| First Layer: | | |
| 1. | Propranolol HCl | 5.31 |
| 2. | Hydroxypropylmethylcellulose | 7.97 |
| 3. | Lactose anhydrous (DCL 21) | 14.60 |
| 4. | Talc | 0.270 |
| 5. | Magnesium stearate | 0.270 |
| Second Layer: | | |
| 1. | Lactose anhydrous (DCL 21) | 21.24 |
| 2. | Magnesium stearate | 0.270 |
| 3. | Talc | 0.270 |
| Third Layer: | | |
| 1. | Propranolol HCl | 7.97 |
| 2. | Hydroxypropylmethylcellulose | 11.95 |
| 3. | Lactose anhydrous (DCL 21) | 17.26 |
| 4. | Talc | 0.270 |
| 5. | Magnesium stearate | 0.270 |
| Coating | | |
| 1. | Eudragit ® L30D-55* | 5.86 |
| 2. | Polyvinylpyrrolidone | 1.47 |
| 3. | Triethyl citrate | 0.88 |
| 4. | Talc | 0.59 |
| 5. | Purified water | Qs |
| Immediate release drug release layer | | |
| 1. | Propranolol HCl | 2.66 |
| 2. | Hydroxypropylmethylcellulose | 0.66 |
| 3. | Aqueous/non-aqueous vehicle | qs |

Process
First Layer:
1. Sieve propranolol HCl, hydroxypropylmethylcellulose and lactose and blend them together.
2. Then pass talc and magnesium stearate through sieve and transfer the mixture to the blender of step 1.
Second Layer:
1. Sieve lactose, talc and magnesium stearate and then blend them together.

Third Layer:
1. Sift propranolol HCl, hydroxypropylmethylcellulose and lactose and blend them with each other.
2. Then pass talc and magnesium stearate through sieve and transfer the mixture to the blender of step 1.

Finally, compress all three layers into a tablet.

Coating:
1. Disperse talc in purified water.
2. Add polyvinylpyrrolidone and triethyl citrate to the mixture of step 1.
3. Further add Eudragit® L30D-55 to the above dispersion while stirring slowly.
4. Then coat the compressed tablets using the coating dispersion of step 3.

Drug Layering Process:
1. Disperse propranolol HCl in aqueous/non-aqueous vehicle.
2. Add hydroxypropylmethylcellulose to the mixture of step 1.
3. Then coat the delayed-release tablets using the coating dispersion of step 2.

Example 6

| S. No. | Ingredients | Percent (%) w/w (total weight of the dosage form) |
|---|---|---|
| | First Layer: | |
| 1. | Fexofenadine | 12.48 |
| 2. | Hydroxypropylmethylcellulose | 10.40 |
| 3. | Lactose | 6.24 |
| 4. | Talc | 0.42 |
| | Second Layer: | |
| 1. | Lactose | 14.57 |
| | Third Layer: | |
| 1. | Pseudoephedrine HCl | 24.97 |
| 2. | Hydroxypropylmethylcellulose | 16.65 |
| 3. | Lactose | 6.24 |
| 4. | Talc | 0.62 |
| | Coating: | |
| 1. | Eudragit ® L30D-55* | 5.49 |
| 2. | Triethyl citrate | 1.37 |
| 3. | Talc | 0.55 |
| 4. | Purified water | Qs |

Process
First Layer:
1. Pass fexofenadine, hydroxypropylmethylcellulose and lactose through a sieve and blend them together.
2. Pass talc through a sieve and transfer to the blender of step 1.

Second Layer:
1. Pass lactose through a sieve.

Third Layer:
1. Pass pseudoephedrine HCl, hydroxypropylmethylcellulose and lactose through a sieve and then blend them together.
2. Then pass talc through a sieve and transfer to the blender of step 1. Finally, compress all three layers into a tablet.

Coating:
1. Disperse talc in purified water.
2. Add triethyl citrate to the mixture of step 1.
3. Further add Eudragit® L30D-55 to the above dispersion while stirring slowly.
4. Then coat the compressed tablets using the coating dispersion of step 3.
5. Finally, drill the orifice on one of the sides of the coated tablet.

Example 7

| S. No. | Ingredients | Percent (%) w/w (total weight of the dosage form) |
|---|---|---|
| | First Layer: | |
| 1. | Diltiazem HCl | 10.76 |
| 2. | Hydroxypropylmethylcellulose | 10.25 |
| 3. | Lactose | 7.54 |
| 4. | Ferric oxide red | 0.15 |
| 5. | Talc | 0.51 |
| | Second Layer: | |
| 1. | Lactose | 25.63 |
| | Third Layer: | |
| 1. | Diltiazem HCl | 19.99 |
| 2. | Hydroxypropylmethylcellulose | 12.81 |
| 3. | Lactose | 4.93 |
| 4. | Ferric oxide yellow | 0.19 |
| 5. | Talc | 0.77 |
| | Coating: | |
| 1. | Eudragit ® L30D-55* | 3.91 |
| 2. | Triethyl citrate | 0.98 |
| 3. | Povidone | 1.17 |
| 4. | Talc | 0.39 |
| 5. | Purified water | Qs |

Process

First Layer:
1. Diltiazem HCl, hydroxypropylmethylcellulose and lactose were passed through a sieve and then blended together.
2. Then ferric oxide red and talc were passed through a sieve and were transferred to the blender of step 1.

Second Layer:
1. Lactose was passed through a sieve.

Third Layer:
1. Diltiazem HCl, hydroxypropylmethylcellulose and lactose were passed through a sieve and then blended together.
2. Then ferric oxide yellow and talc were passed through a sieve and was transferred to the blender of step 1.

Finally, all three layers were compressed into a tablet.

Coating:
1. Talc was dispersed in purified water.
2. Then povidone was added to the talc suspension of step 1.
3. Methyl citrate was added to the mixture of step 2.
4. Further Eudragit® L30D-55 was added to the above dispersion while stirring slowly.
5. The compressed tablets were coated using the coating dispersion of step 4.
6. Finally, an orifice was drilled on one of the sides of the coated tablet.

Example 8

| S. No. | Ingredients | Percent (%) w/w (total weight of the dosage form) |
|---|---|---|
| | First Layer: | |
| 1. | Simvastatin | 1.57 |
| 2. | Hydroxypropylmethylcellulose | 5.91 |
| 3. | Lactose | 7.79 |
| 4. | Ferric oxide red | 0.08 |
| 5. | Talc | 0.16 |
| | Second Layer: | |
| 1. | Lactose | 14.96 |
| 2. | Povidone | 0.79 |
| | Third Layer: | |
| 1. | Niacin | 39.37 |
| 2. | Hydroxypropylmethylcellulose | 15.75 |
| 3. | Lactose | 5.35 |
| 4. | Ferric oxide yellow | 0.31 |
| 5. | Talc | 0.55 |
| | Coating: | |
| 1. | Eudragit ® L30D-55* | 5.49 |
| 2. | Triethyl citrate | 1.37 |
| 3. | Talc | 0.55 |
| 4. | Purified water | Qs |

Process
First Layer:
1. Simvastatin, hydroxypropylmethylcellulose and lactose were passed through a sieve and then blended together.
2. Then ferric oxide red and talc were passed through a sieve and were transferred to the blender of step 1.
Second Layer:
1. Lactose and povidone were passed through a sieve and blended together.
Third Layer:
1. Niacin, hydroxypropylmethylcellulose and lactose were passed through a sieve and then blended together.
2. Then ferric oxide yellow and talc were passed through a sieve and were transferred to the blender of step 1.
Finally, all three layers were compressed into a tablet.
Coating:
1. Talc was dispersed in purified water.
2. Methyl citrate was added to the mixture of step 1.
3. Further Eudragit® L30D-55 was added to the above dispersion while stirring slowly.
4. The compressed tablets were coated using the coating dispersion of step 3.
5. Finally, an orifice was drilled on both sides of the coated tablet.

The invention claimed is:

1. A tri-layered tablet having a coating, comprising three layers wherein:
   a) a first layer and a third layer contain at least one active pharmaceutical ingredient; and
   b) a second layer is either a placebo layer or contains an active pharmaceutical ingredient;
wherein the orientation of the layers is stacked such that the first layer and the third layer constitute the top and bottom layers respectively, and the second layer is the middle layer of the tri-layered tablet and the coating on the tablet is a delayed release coating;
wherein after reaching the intestine the delayed release coating and the second layer dissolve immediately thereby separating the first and the third layers.

2. The tri-layered coated tablet according to claim 1, wherein the first layer and the third layer contain the same drug.

3. The tri-layered coated tablet according to claim 1, wherein the first layer and the third layer contain different drugs.

4. The tri-layered coated tablet according to claim 1, wherein the first layer and the third layer provide an extended-release of the drug contained therein.

5. The tri-layered coated tablet according to claim 1, wherein the first layer provides an immediate-release of the drug and the third layer provides an extended-release of the drug contained therein after reaching the intestine and dissolution of the delayed release coating.

6. The tri-layered coated tablet according to claim 1, wherein the second layer comprises lactose and optionally a drug.

7. The tri-layered coated tablet according to claim 6, wherein the first layer, the second layer and the third layer contain the same drug.

8. The tri-layered coated tablet according to claim 6, wherein the first layer, the second layer and the third layers contain different drugs.

9. The tri-layered coated tablet according to claim 6, wherein the first layer and the second layer contain the same drug and the third layer contains a different drug.

10. The tri-layered coated tablet according to claim 6, wherein the first layer provides an immediate-release of the drug and the third layer provides an extended-release of the drug after reaching the intestine and dissolution of the delayed release coating, provided that the drugs in the first layer and the second layers are different.

11. The tri-layered coated tablet according to claim 1, wherein the delayed-release coating contains an orifice on either the top or the bottom layer of the tablet.

12. The tri-layered coated tablet according to claim 1, wherein the delayed-release coating contains orifices on both the top and the bottom layers of the tablet.

13. The tri-layered coated tablet according to claim 1, wherein the delayed-release coating contains one or more pore-forming agents.

14. The tri-layered coated tablet according to claim 1, wherein the delayed-release coating contains an orifice on either the top or the bottom layer of the tablet and a pore-forming agent.

15. The tri-layered coated tablet according to claim 1, wherein the delayed-release coating contains orifices on both the top and the bottom layers of the tablet and a pore-forming agent.

16. The tri-layered coated tablet according to claim 13 or 14, wherein the pore-forming agent used in the delayed-release coating is a hydrophilic substance, and is selected from the group consisting of sodium chloride, potassium chloride, and magnesium salts, lactose, sucrose, sorbitol, and mannitol, polyethylene glycol and propylene glycol; hydroxypropyl cellulose, hydroxy propyl methylcellulose; methacrylic acid copolymers; sodium starch glycolate, polyvinylpyrrolidones, carbopol, xanthan gum; and mixtures thereof.

17. The tri-layered coated tablet according to claim 1, wherein the delayed-release polymer used in the delayed-release coating is selected from the group consisting of cellulose acetate phthalate (CAP), cellulose acetate trimelletate (CAT), poly(vinyl acetate)phthalate (PVAP), hydroxypropyl methylcellulose phthalate (HPMCP), poly(methacrylate ethylacrylate) (1:1) copolymer (MA-EA), poly (methacrylate methylmethacrylate) (1:1) copolymer (MA- MMA), poly(methacrylate methylmethacrylate) (1:2) copolymer, Poly(methyl acrylate-co-methyl methacrylate-co-methacrylic acid) 7:3:1, hydroxypropyl methylcellulose acetate succinate (HPMCAS), and combinations thereof.

18. The tri-layered coated tablet according to claim 1, wherein the delayed-release coating further comprises an immediate-release drug layer over it.

19. The tri-layered coated tablet according to claim 18, wherein the immediate-release drug layer over the delayed-release coating layer contains the same drug as that of one of the first layer, the second layer, or the third layer of the tablet.

20. The tri-layered coated tablet according to claim 18, wherein the immediate-release layer over the delayed-release coating layer contains a drug different than that of one of the first layer, the second layer, or the third layer of the tablet.

21. The tri-layered coated tablet according to claim 1, wherein the tablet further comprises pharmaceutically acceptable excipients selected from the group consisting of adsorbents, antioxidants, acidifying agents, alkalizing agents, buffering agents, colorants, flavorants, sweetening agents, antiadherents, binders, diluents, direct compression excipients, disintegrants, glidants, lubricants, opaquants, and polishing agents.

\* \* \* \* \*